United States Patent [19]
Glandorf

[11] Patent Number: 5,820,854
[45] Date of Patent: Oct. 13, 1998

[54] ORAL COMPOSITIONS CONTAINING POLYOXYETHYLENE

[75] Inventor: William Michael Glandorf, Mason, Ohio

[73] Assignee: The Procter & Gamble Company, Cincinnati, Ohio

[21] Appl. No.: 829,491

[22] Filed: Mar. 27, 1997

[51] Int. Cl.$^6$ ........................................ A61K 7/18
[52] U.S. Cl. .............................. 424/52; 424/49; 424/53; 424/57
[58] Field of Search ........................................ 424/49–88

[56] References Cited

U.S. PATENT DOCUMENTS

| | | | |
|---|---|---|---|
| 2,677,700 | 5/1954 | Jackson et al. | 260/488 |
| 2,773,801 | 12/1956 | Fox | 424/49 |
| 2,991,229 | 7/1961 | Ivison | 424/49 |
| 3,020,230 | 2/1962 | Smith | 210/54 |
| 3,906,090 | 9/1975 | Colodney | 424/52 |
| 3,911,104 | 10/1975 | Harrison | 424/52 |
| 3,954,962 | 5/1976 | Prussin et al. | 424/149 |
| 4,383,987 | 5/1983 | Kiozpeoplou | 424/49 |
| 4,407,788 | 10/1983 | Kiozpeoplou | 424/49 |
| 4,687,663 | 8/1987 | Schaeffer | 424/53 |
| 5,171,564 | 12/1992 | Nathod et al. | 424/153 |
| 5,252,577 | 10/1993 | Breuer et al. | 514/270 |
| 5,292,502 | 3/1994 | Burke et al. | 424/54 |
| 5,565,190 | 10/1996 | Santalucia et al. | 424/53 |
| 5,599,525 | 2/1997 | Hsu et al. | 424/53 |
| 5,599,527 | 2/1997 | Hsu et al. | 424/53 |
| 5,614,174 | 3/1997 | Hsu et al. | 424/53 |

*Primary Examiner*—Shep K. Rose
*Attorney, Agent, or Firm*—Angela Marie Stone; Mary Catherine Hentz; Douglas C. Mohl

[57] ABSTRACT

The present invention relates a dentifrice formulation contained in physically separated compartments of a dispenser, comprising a first dentifrice composition having an ionic strength of from about 1,000 $\mu$mho to about 50,000 $\mu$mho comprising from about 0.1% to about 8% of a polyoxyethylene having a molecular weight of from about 200,000 to about 7,000,000 and from about 92% to about 99.5% of one or more aqueous carriers; and a second dentifrice composition. The present invention also relates to a dentifrice formulation contained in physically separated compartments of a dispenser, comprising a first dentifrice composition having an ionic strength of from about 1,000 $\mu$mho to about 50,000 $\mu$mho; and a second dentifrice composition comprising from about 0.1% to about 8% of a polyoxyethylene having a molecular weight of from about 200,000 to about 7,000,000 and from about 92% to about 99.9% of one or more aqueous carriers. The present invention also relates to a dentifrice composition having an ionic strength of from about 1,000 $\mu$mho to about 50,000 $\mu$mho comprising from about 0.1% to about 8% of a polyoxyethylene having a molecular weight of from about 200,000 to about 7,000,000 and from about 92% to about 99.9% of one or more aqueous carriers.

20 Claims, No Drawings

ORAL COMPOSITIONS CONTAINING POLYOXYETHYLENE

BACKGROUND OF THE INVENTION

The present invention relates to high ionic strength dentifrice formulations which contain high molecular weight polyoxyethylene. The dentifrice formulation may contain two separate dentifrice compositions or a single dentifrice composition.

Polyoxyethylene may alternatively be called polyethylene glycol or poly(ethylene oxide). The use of polyoxyethylene in a dentifrice is known in the art. However, most polyoxyethylene or polyethylene glycols used in dentifrice formulations have a relative low molecular weight, generally from about 200 to about 700. The use of high molecular weight polyoxyethylene is found in U.S. Pat. No. 2,991,229 issued Jul. 4, 1961 where poly(ethylene oxide) is used as a replacement for the natural gums in toothpaste. U.S. Pat. No. 4,383,987 issued May 17, 1983 discloses a foaming dentifrice comprising liquid humectant, xanthan gum, and a polyoxyethylene-polyoxypropylene block copolymer. Resinous poly (ethylene oxide) is an optional ingredient. U.S. Pat. No. 4,407,788 issued Oct. 4, 1983 discloses the dentifrice in which siliceous polishing material flocculate in the presence of resinous poly(ethylene oxide) to provide desirable stain removal. Although these disclosures are known, the present inventor has discovered the polyoxyethylene can be used without a polyoxyethylene-polyoxypropylene block copolymer to provide a high foaming dentifrice. Additionally, the polyoxyethylene containing dentifrice of the present invention can be formulated without silica. If the dentifrice is formulated with silica, flocculation of the silica around the polyoxyethylene is not thought to occur.

It is known that dentifrice formulations with high ionic strength have low foam volume and a poor quality of foam. The high ionic strength will occur in dentifrice compositions containing high salt levels. Commonly used salts include bicarbonate, carbonate, sodium chloride, the tartar control agents such as pyrophosphates and polyphosphates, among others. The present inventor has discovered that a dentifrice with a high ionic strength can be made with improved sensory attributes by the addition of polyoxyethylene. By adding polyoxyethylene to the dentifrice formulation with a high ionic strength, the dentifrice provides an increased foam volume, increased foam viscosity, and a smooth teeth feeling. In a dual phase dentifrice, the high molecular weight polyoxyethylene may be present in a dentifrice composition with high ionic strength or the polyoxyethylene may be present in a dentifrice composition which is dispensed side-by-side with the high ionic strength dentifrice.

It is an object of the present invention to provide stable dentifrice formulations having high ionic strength and improved sensory attributes. It is an object of the present invention to provide a dentifrice composition with a high ionic strength comprising a polyoxyethylene having a molecular weight of from about 200,000 to about 7,000,000. This composition may be a single dentifrice composition or one composition of a dual phase product. It is also an object of the present invention to provide a first dentifrice composition having a high ionic strength and a second dentifrice composition comprising a polyoxyethylene having a molecular weight of from about 200,000 to about 7,000,000. It is also an object of the present invention to provide dentifrice formulations with antitartar activity through the use of tartar control agents.

These and other objects of the present invention will become readily apparent from the detailed description which follows.

All percentages and ratios used herein are by weight of the specific dentifrice composition and not of the overall dentifrice formulation that is delivered, unless otherwise specified. All measurements are made at 25° C., unless otherwise specified.

SUMMARY OF THE INVENTION

The present invention relates a dentifrice formulation contained in physically separated compartments of a dispenser, comprising a first dentifrice composition having an ionic strength of from about 1,000 $\mu$mho to about 50,000 $\mu$mho comprising from about 0.1% to about 8% of a polyoxyethylene having a molecular weight of from about 200,000 to about 7,000,000 and from about 92% to about 99.5% of one or more aqueous carriers; and a second dentifrice composition. The present invention also relates to a dentifrice formulation contained in physically separated compartments of a dispenser, comprising a first dentifrice composition having an ionic strength of from about 1,000 $\mu$mho to about 50,000 $\mu$mho; and a second dentifrice composition comprising from about 0.1% to about 8% of a polyoxyethylene having a molecular weight of from about 200,000 to about 7,000,000 and from about 92% to about 99.9% of one or more aqueous carriers. The present invention also relates to a dentifrice composition having an ionic strength of from about 1,000 $\mu$mho to about 50,000 $\mu$mho comprising from about 0.1% to about 8% of a polyoxyethylene having a molecular weight of from about 200,000 to about 7,000,000 and from about 92% to about 99.9% of one or more aqueous carriers.

DETAILED DESCRIPTION OF THE INVENTION

The dentifrice formulation of the present invention may be in the form of a toothpaste or dentifrice. The term "dentifrice formulation" as used herein means the total dentifrice that is delivered to the oral surfaces. The dentifrice formulation may be a combination of the two or more dentifrice compositions or may be a single dentifrice composition. The dentifrice formulation is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. The dentifrice composition may be contained in a physically separated compartment of a dispenser and dispensed side-by-side or may be a single composition.

The term "dispenser", as used herein, means any pump, tube, or container suitable for dispensing dentifrice.

The term "aqueous carrier" as used herein means any safe and effective materials for use in the compositions of the present invention. Such materials include abrasive polishing materials, propylene glycol, acidic compounds, calcium peroxide, buffering agent, thickening materials, humectants, water, surfactants, titanium dioxide, flavor system, coolants, sweetening agents, xylitol, coloring agents, antimicrobial agents, and mixtures thereof.

The present compositions comprise essential components, as well as optional components. The essential and optional components of the compositions of the present invention are described in the following paragraphs.

Polyoxyethylene

The dentifrice formulation of the present invention will include a polyoxyethylene. The first and/or second dentifrice compositions may contain the polyoxyethylene. Polyoxyethylene is also commonly known as polyethylene glycol ("PEG") or polyethylene oxide. The polyoxyethylenes suitable for this invention will have a molecular weight of from about 200,000 to about 7,000,000. Preferably, the molecular weights will be from about 600,000 to about 2,000,000, and more preferably from about 800,000 to about 1,000,000. "Polyox" is the tradename for the high molecular weight polyoxyethylene produced by Union Carbide. The polyoxyethylene is present in an amount of from about 0.1% to about 8%, preferably from about 0.2% to about 5%, and more preferably from about 0.3% to about 2%, by weight of the dentifrice composition.

Ionic Strength

High ionic strength in dentifrice compositions will occur when the dentifrice contains ingredients having an ionic character. Commonly used ingredients with ionic character include materials such as salts and surfactants. Dentifrices with high salt levels and/or high surfactant levels will have a high ionic strength. Commonly used salts in dentifrices include bicarbonate, carbonate, sodium chloride, and tartar control agents such as pyrophosphates and polyphosphates, among others. Ionic strength of a dentifrice is measured by conductivity of the dilute slurry. The slurry is a 3:1 water to dentifrice slurry. High ionic strength is defined as a dentifrice having an ionic strength of from about 1,000 $\mu$mho to about 50,000 $\mu$mho. Preferably the dentifrice will have an ionic strength of from about 5,000 $\mu$mho to about 40,000 $\mu$mho and more preferably from about 10,000 $\mu$mho to about 25,000 $\mu$mho. The total salt level of dentifrices with high ionic strength is generally from about 4% to about 70%, preferably from about 6% to about 60%, and more preferably from about 8% to about 50%.

Alkali Metal Bicarbonate Salt

The first dentifrice composition of the present invention with a high ionic strength may include an alkali metal bicarbonate salt which contributes to the high salt level. Sodium bicarbonate, also known as baking soda, is the preferred alkali metal bicarbonate salt. The present composition may contain from about 4% to about 50%, preferably from about 6% to about 30%, more preferably from about 8% to about 20%, and most preferably from about 8% to about 18% of an alkali metal bicarbonate salt, by weight of the dentifrice composition.

Tartar Control Agents

The present invention may include a tartar control agent. The tartar control agent will likely contribute the high ionic strength and high salt level. The tartar control agent is preferably present in the first dentifrice composition, but may be present in the first and/or second dentifrice compositions. The tartar control agent may be any materials known to be effective in reducing calcium phosphate mineral deposition related to calculus formation. The preferred tartar control agent is selected from the group consisting of a polyphosphate source, tripolyphosphate source, a pyrophosphates, and mixtures thereof.

The pyrophosphate salts useful in the present compositions include the di and tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. Compositions comprising pyrophosphate typically containing from about 1% to about 15%, preferably from about 2% to about 10%, and most preferably from about 2% to about 8%, by weight of the composition. The pyrophosphate salts are described in U.S. Pat. No. 4,515,772, issued May 7, 1985, and U.S. Pat. No. 4,885,155, issued Dec. 5, 1989, both to Parran et al., incorporated herein by reference in their entirety, as well as the references disclosed therein.

The present invention may include a polyphosphate source. A polyphosphate is generally understood to consist of two or more phosphate molecules arranged primarily in a linear configuration, although some cyclic derivatives may be present. The inorganic polyphosphate salts desired include sodium tripolyphosphate, tetrapolyphosphate, and hexametaphosphate, among others. Polyphosphates larger than tetrapolyphosphate usually occur as amorphous glassy materials. Preferred are polyphosphates manufactured by FMC Corporation which are commercially known as Sodaphos ($n \approx 6$), Hexaphos ($n \approx 13$), and Glass H ($n \approx 21$). The polyphosphate source will typically comprise from about 0.5% to about 20%, preferably from about 4% to about 15%, more preferably from about 6% to about 10%, and most preferably from about 7% to about 9%, by weight of the dentifrice composition.

The phosphate sources are described in more detail in Kirk & Othmer, *Encyclopedia of Chemical Technology*, Fourth Edition, Volume 18, Wiley-Interscience Publishers (1996), pages 685–707, incorporated herein by reference in its entirety, including all references incorporated into Kirk & Othmer. Optional agents to be used in place of or in combination with the polyphosphate or pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, diphosphonates (e.g., EHDP; AHP), polypeptides (such as polyaspartic and polyglutamic acids), and mixtures thereof.

Fluoride Ion Source

The first and/or second dentifrice compositions of the present invention may incorporate a soluble fluoride ion source capable of providing free fluoride ions. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety. The fluoride ion source should be capable of providing from about 50 ppm to about 3500 ppm, and preferably from about 500 ppm to about 3000 ppm of free fluoride ions.

Aqueous Carriers

In preparing the present compositions, it is desirable to add one or more aqueous carriers to the dentifrice compositions. Such materials are well known in the art and are readily chosen by one skilled in the art based on the physical and aesthetic properties desired for the compositions being prepared. Aqueous carriers typically comprise from about 10% to about 99%, preferably from about 40% to about 98%, and more preferably from about 60% to about 95%, by weight of the dentifrice composition.

Abrasive Polishing Materials

An abrasive polishing material may also be included in one or both of the dentifrice compositions. The abrasive polishing material contemplated for use in the compositions of the present invention can be any material which does not excessively abrade dentin. Typical abrasive polishing materials include silicas including gels and precipitates; aluminas; phosphates including orthophosphates, polymetaphosphates, and insoluble pyrophosphates; and mixtures thereof. Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, and in Rice, U.S. Pat. No. 5,589,160, issued Dec. 31, 1996, incorporated herein by reference. Silica abrasives described in U.S. patent applications, Ser. Nos. 08/434,147 and 08/434,154, both filed May 2, 1995, are also herein incorporated by reference. The abrasive in the toothpaste compositions described herein is generally present at a level of from about 6% to about 70% by weight of the composition. Preferably, toothpastes contain from about 10% to about 50% of abrasive, by weight of the dentifrice composition.

Propylene Glycol

The first and/or second dentifrice compositions may also comprise propylene glycol. The propylene glycol is suitable for use on the skin and mucosal surfaces such as in the oral cavity. The first dentifrice composition may contain from about 0.5% to about 30%, preferably from about 1% to about 20%, and more preferably from about 2% to about 15% of propylene glycol, by weight of the dentifrice composition.

Acidic Compound

The second dentifrice composition of the present invention may incorporate an acidic compound. The acidic compound may be organic or inorganic. The acidic compound may be any material which will be a proton donor that is capable of neutralizing bicarbonate. Acidic compounds suitable for use include carboxylic acids, phosphoric acids, alpha-hydroxy acids, sulfonic acids, and mixture thereof. Specific acids include citric acid, malic acid, alginic acid, succinic acid, lactic acid, tartaric acid, glycolic acid, adipic acid, potassium bitartrate acid, acid sodium citrate, phosphoric acid, boric acid, and acid phosphate and pyrophosphate salts. A blend of acids are preferred. Citric acid and malic acid are preferred. Acid anhydrides and acid salts of the above acids may also be used. Suitable salts include mono or disodium salts of citric acid, mono sodium salts of malic acid, and mixtures thereof. The second dentifrice composition may contain from about 0.5% to about 20%, preferably from about 1% to about 15%, and more preferably from about 4% to about 12% of an acidic compound, by weight of the dentifrice composition.

Calcium Peroxide

The present invention may include calcium peroxide in the first and/or second dentifrice composition. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Buffering Agent

The dentifrice compositions may each contain a buffering agent. Buffering agents, as used herein, refer to agents that can be used to adjust the pH of the compositions. The buffering agents suitable include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, sodium acid pyrophosphate, sodium citrate, and sodium malate. Buffering agents are used at a level of from about 0.1% to about 30%, preferably from about 1% to about 10%, and more preferably from about 1.5% to about 3%, by weight of the dentifrice composition.

Additional Aqueous Carriers

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, mineral oil, polyethylene glycol, and other edible polyhydric alcohols. The polyethylene glycol may have a molecular weight of from about 200 to about 7000. The humectant generally comprises from about 0% to 70%, and preferably from about 15% to 55%, by weight of the dentifrice composition.

Water employed in the preparation of commercially suitable dentifrice compositions should preferably be of low ion content and free of organic impurities. In the first or second dentifrice compositions, water will generally comprise from about 5% to about 70%, and preferably from about 10% to about 50%, by weight of the composition herein. Alternatively, the first dentifrice composition may comprise a lower level of water, generally from about 5% to about 20%, preferably from about 7% to about 14%, and more preferably from about 7% to about 12%, by weight of the dentifrice composition. The lower level of water is preferred in compositions comprising polyphosphates. The amounts of water include the free water which is added plus that which is introduced with other materials, such as with sorbitol, silica, surfactant solutions, and/or color solutions.

The present compositions may also comprise surfactants, also commonly referred to as sudsing agents. The surfactants may contribute to the high ionic strength of a dentifrice. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate). Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Many suitable surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. A flavor system is generally used in the compositions at levels of from about 0.001% to about 5%, by weight of the composition.

Coolants may also be part of the flavor system or added separately to the composition. Preferred coolants in the present compositions are the paramenthan carboxyamide agents such as N-ethyl-p-menthan-3-carboxamide (known commercially as "WS-3"), menthol, 3-1-menthoxypropane-1,2-diol ("TK-10"), menthone glycerol acetal ("MGA"), menthyl lactate, and mixtures thereof. A coolant is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents and water soluble antimicrobials, such as quaternary ammonium salts and bis-biquanide salts, among others. Triclosan monophosphate is an additional water soluble antimicrobial agent. Other compounds are bis[4-(R-amino)-1-pyridinium] alkanes as disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. These agents may be present at levels of from about 0.01% to about 1.5%, by weight of the dentifrice composition.

The dentifrice formulation may contain a first and second dentifrice composition or only a single dentifrice composition. If there are two dentifrice compositions, the first and second dentifrice compositions will be physically separated in a dentifrice dispenser. The dentifrice compositions may be a paste, gel, or any configuration or combination thereof. It is preferred that the first dentifrice composition be a paste and the second dentifrice composition be a gel. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the dentifrice formulation may be delivered from a kit containing two separate dispensers which are used to deliver two dentifrice compositions that are both used simultaneously.

Method of Treatment

The method of treatment herein comprises contacting the dental enamel surfaces in the mouth with the dentifrice compositions according to the present invention.

Examples & Method of Manufacturing

The following examples further describe and demonstrate embodiments within the scope of the present invention. These examples are given solely for the purpose of illustration and are not to be construed as limitations of the present invention as many variations thereof are possible without departing from the spirit and scope.

EXAMPLE I

| First Dentifrice Composition | | Second Dentifrice Composition | |
|---|---|---|---|
| Ingredient | Wt. % | Ingredient | Wt. % |
| Carboxymethylcellulose | 0.40 | Color | 0.30 |
| Water | 5.00 | Water | 32.08 |
| Flavor | 1.00 | Flavor | 1.00 |
| Glycerin | 36.00 | Glycerin | 44.14 |
| Polyoxyethylene | 0.50 | Poloxamer 407 | 20.00 |
| Propylene Glycol | 9.00 | Trisodium Phosphate | 0.48 |
| Sodium Alkyl Sulfate[a] | 5.00 | Sodium Saccharin | 0.40 |
| Silica | 20.00 | Coolant | 0.60 |
| Sodium Carbonate | 1.90 | Sodium Phosphate | 0.52 |
| Sodium Saccharin | 0.40 | Sodium Fluoride | .48 |
| Sodium Bicarbonate | 9.00 | | |
| Titanium Dioxide | 1.00 | | |
| Xanthan Gum | 0.20 | | |
| Glass H Polyphosphate | 4.00 | | |
| Polyethylene Glycol | 5.00 | | |
| Calcium Peroxide | 1.00 | | |
| Coolant | 0.60 | | |

[a]27.9% solution

The first dentifrice composition is prepared as follows. Add the water and saccharin to a mixing vessel. Disperse the thickening agents, carboxymethyl cellulose and xanthan gum, in the glycerin. Add this mixture of dispersed thickening agents in glycerin to the mixing vessel and mix well. Add the flavor, coolant, polyoxyethylene, polyethylene glycol, propylene glycol, titanium dioxide, and sodium alkyl sulfate to the mixture and mix well. Next add the sodium carbonate and the silica. After mixing, add the sodium bicarbonate. Finally, add the polyphosphate and calcium peroxide. Continue stirring the mixture until homogeneous.

The second dentifrice composition is prepared as follows. Add the water, saccharin, fluoride, glycerin, and Poloxamer to the mixing vessel. Heat the solution to at least 70° C., and mix until the Poloxamer melts. Allow the batch to cool and add the flavor, coolant, color, sodium phosphate, and trisodium phosphate. Mix until homogeneous.

EXAMPLE II

| First Dentifrice Composition | | Second Dentifrice Composition | |
|---|---|---|---|
| Ingredient | Wt. % | Ingredient | Wt. % |
| Carboxymethylcellulose | 0.40 | Color | 0.30 |
| Water | 5.00 | Water | 26.52 |
| Flavor | 1.00 | Flavor | 1.00 |
| Glycerin | 33.40 | Glycerin | 9.00 |
| Poloxamer 407 | 3.00 | Sorbitol[c] | 20.00 |
| Propylene Glycol | 8.50 | Polyoxyethylene | 1.00 |
| Sodium Alkyl Sulfate[a] | 4.00 | Sodium Saccharin | 0.35 |
| Silica | 20.50 | Coolant | 0.60 |
| Sodium Carbonate | 2.00 | Mineral Oil | 1.00 |
| Sodium Saccharin | 0.40 | Sodium Fluoride | 0.48 |
| Sodium Bicarbonate | 12.00 | Citric Acid | 10.00 |
| Titanium Dioxide | 1.00 | Carboxymethylcellulose | 0.50 |
| Xanthan Gum | 0.20 | Xanthan Gum | 0.25 |
| Glass H Polyphosphate | 4.00 | Polyethylene Glycol | 3.00 |
| Polyethylene Glycol | 3.00 | Sodium Alkyl Sulfate[a] | 6.00 |
| Coolant | 0.60 | Silica | 20.00 |
| Polyoxyethylene | 1.00 | | |

[a]27.9% solution
[c]70% solution

The first dentifrice composition is prepared as follows. Add the water and saccharin to a mixing vessel. Disperse the thickening agents, carboxymethyl cellulose and xanthan gum, in the glycerin. Add this mixture of dispersed thickening agents in glycerin to the mixing vessel and mix well. Add the flavor, coolant, Poloxamer, polyoxyethylene, polyethylene glycol, propylene glycol, titanium dioxide, and sodium alkyl sulfate to the mixture and mix well. Next add the sodium carbonate and the silica. After mixing, add the sodium bicarbonate. Finally, add the polyphosphate. Continue stirring the mixture until homogeneous.

The second dentifrice composition is prepared as follows. Add the water, saccharin, fluoride, sorbitol, mineral oil, polyethylene glycol, polyoxyethylene, color, and citric acid to the mixing vessel. Disperse the thickening agents, carboxymethyl cellulose and xanthan gum, in the glycerin. Add this mixture of dispersed thickening agents in glycerin to the mixing vessel and mix well. Add the flavor, coolant, and sodium alkyl sulfate. Finally, add the silica into the mixture and mix well. Continue stirring the mixture until homogeneous.

EXAMPLE III

| First Dentifrice Composition | | Second Dentifrice Composition | |
|---|---|---|---|
| Ingredient | Wt. % | Ingredient | Wt. % |
| Carboxymethylcellulose | 0.40 | Color | 0.30 |
| Water | 5.00 | Water | 48.00 |
| Flavor | 1.60 | Flavor | 1.60 |
| Glycerin | 32.40 | Glycerin | 39.00 |
| Poloxamer 407 | 3.00 | Carbopol | 2.80 |
| Propylene Glycol | 8.00 | Sodium Hydroxide[b] | 1.00 |
| Sodium Alkyl Sulfate[a] | 4.00 | Sodium Saccharin | 0.40 |
| Silica | 19.00 | Sodium, Alkyl Sulfate[a] | 2.00 |
| Sodium Carbonate | 2.00 | Betaine | 2.90 |
| Sodium Saccharin | 0.40 | Polyoxyethylene | 2.00 |
| Sodium Bicarbonate | 9.00 | | |
| Titanium Dioxide | 1.00 | | |
| Xanthan Gum | 0.20 | | |
| Glass H Polyphosphate | 10.00 | | |
| Polyethylene Glycol | 3.00 | | |
| Calcium Peroxide | 1.00 | | |

[a]27.9% solution
[b]5.0% solution

EXAMPLE IV

| First Dentifrice Composition | | Second Dentifrice Composition | |
|---|---|---|---|
| Ingredient | Wt. % | Ingredient | Wt. % |
| Carboxymethylcellulose | 0.40 | Color | 0.30 |
| Water | 5.00 | Water | 47.52 |
| Flavor | 0.90 | Flavor | 0.80 |
| Glycerin | 34.00 | Glycerin | 39.00 |
| Poloxamer 407 | 3.00 | Carbopol | 2.60 |
| Propylene Glycol | 8.00 | Sodium Hydroxide[b] | 1.00 |
| Sodium Alkyl Sulfate[a] | 4.00 | Sodium Saccharin | 0.40 |
| Silica | 19.00 | Sodium Alkyl Sulfate[a] | 2.00 |
| Sodium Carbonate | 2.00 | Betaine | 2.90 |
| Sodium Saccharin | 0.40 | Polyoxyethylene | 3.00 |
| Sodium Bicarbonate | 9.00 | Sodium Fluoride | 0.48 |
| Titanium Dioxide | 1.00 | | |
| Xanthan Gum | 0.25 | | |
| Glass H Polyphosphate | 10.00 | | |
| Polyethylene Glycol | 3.00 | | |

[a]27.9% solution
[b]50% solution

EXAMPLE V

| First Dentifrice Composition | | Second Dentifrice Composition | |
|---|---|---|---|
| Ingredient | Wt. % | Ingredient | Wt. % |
| Carboxymethylcellulose | 0.40 | Color | 0.30 |
| Water | 5.00 | Water | 48.30 |
| Flavor | 1.60 | Flavor | 1.60 |
| Glycerin | 39.00 | Glycerin | 37.00 |
| Poloxamer 407 | 3.00 | Carbopol | 2.50 |
| Propylene Glycol | 8.00 | Sodium Hydroxide[b] | 1.00 |
| Sodium Alkyl Sulfate[a] | 4.00 | Sodium Saccharin | 0.40 |
| Silica | 22.00 | Sodium Alkyl Sulfate[a] | 2.00 |
| Sodium Carbonate | 2.00 | Betaine | 2.90 |
| Sodium Saccharin | 0.40 | Polyoxyethylene | 4.00 |
| Sodium Bicarbonate | 9.00 | | |
| Titanium Dioxide | 1.00 | | |
| Xanthan Gum | 0.20 | | |
| Polyethylene Glycol | 3.00 | | |
| Calcium Peroxide | 1.00 | | |
| Sodium Fluoride | 0.40 | | |

[a]27.9% solution
[b]50% solution

Examples III, IV, and V are prepared as follows. For the first dentifrice composition, add the water, saccharin, and fluoride to a mixing vessel. Disperse the thickening agents, carboxymethyl cellulose and xanthan gum, in the glycerin. Add this mixture of dispersed thickening agents in glycerin to the mixing vessel and mix well. Add the flavor, Poloxamer, polyoxyethylene, polyethylene glycol, propylene glycol, and titanium dioxide to the mixture and mix well. Next add the sodium carbonate and the silica. After mixing, add the sodium bicarbonate and sodium alkyl sulfate. Finally if required, add the polyphosphate and calcium peroxide. Continue stirring the mixture until homogeneous.

For the second dentifrice composition, add the water, saccharin, color, and fluoride (if required) to the mixing vessel. Heat to at least 40° C. Premix the Carbopol and polyoxyethylene in the glycerin. Add this premix to the mixing vessel and mix well. Premix the flavor and sodium alkyl sulfate until uniform in color and then add the betaine. Add this premix to the mixing vessel and mix well. Add the sodium hydroxide to the mixture and continue to mix until homogeneous.

EXAMPLE VI

| Ingredient | Weight % |
|---|---|
| Sorbitol[c] | 40.04 |
| Glycerin | 7.00 |
| Water | 10.00 |
| Polyoxyethylene | 1.00 |
| Sodium Fluoride | 0.24 |
| Sodium Saccharin | 0.52 |
| Sodium Carbonate | 1.00 |
| Sodium Bicarbonate | 19.00 |
| Carboxymethylcellulose | 0.85 |
| Titanium Dioxide | 0.35 |
| Silica | 15.00 |
| Sodium Alkyl Sulfate[a] | 4.90 |
| Flavor System | 1.00 |

[a]27.9% solution
[c]70% solution

EXAMPLE VII

| Ingredient | Weight % |
|---|---|
| Sorbitol[c] | 13.00 |
| Glycerin | 7.46 |
| Water | 10.00 |
| Polyoxyethylene | 3.00 |
| Sodium Fluoride | 0.24 |
| Sodium Saccharin | 0.50 |
| Sodium Bicarbonate | 60.00 |
| Carboxymethylcellulose | 0.80 |
| Sodium Alkyl Sulfate[a] | 4.00 |
| Flavor System | 1.00 |

[a]27.9% solution
[c]70% solution

Examples VI and VII are prepared as follows. Start by combining water, sorbitol, sodium fluoride, and saccharin. Disperse the thickening agents, carboxymethylcellulose, in the remaining humectant, glycerin, before adding to the mixture. Add the flavor system, polyoxyethylene, titanium dioxide (if required), and sodium alkyl sulfate. Next add the sodium carbonate and silica (if required), and bicarbonate. Continue mixing until homogeneous. Mill and/or deareate the final product if desired for aesthetic preference.

EXAMPLE VIII

| Ingredient | Weight % |
|---|---|
| Sorbitol[c] | 14.11 |
| Glycerin | 15.00 |
| Water | 19.72 |
| Polyoxyethylene | 2.00 |
| Sodium Fluoride | 0.24 |
| Sodium Saccharin | 0.53 |
| Sodium Carbonate | 1.25 |
| Sodium Bicarbonate | 18.00 |
| Carboxymethylcellulose | 0.80 |
| Silica | 15.00 |
| Sodium Alkyl Sulfate[a] | 4.00 |
| Flavor System | 1.00 |
| Color | 0.30 |
| Polyethylene Glycol | 3.00 |
| Tetrasodium Pyrophosphate | 5.05 |

[a]27.9% solution
[c]70% solution

EXAMPLE IX

| Ingredient | Weight % |
| --- | --- |
| Calcium Peroxide | 1.00 |
| Glycerin | 34.13 |
| Water | 4.00 |
| Polyoxyethylene | 3.00 |
| Sodium Fluoride | 0.24 |
| Sodium Saccharin | 0.50 |
| Sodium Carbonate | 2.00 |
| Sodium Bicarbonate | 5.00 |
| Carboxymethylcellulose | 0.20 |
| Xanthan Gum | 0.35 |
| Silica | 23.00 |
| Sodium Alkyl Sulfate(a) | 6.00 |
| Flavor System | 1.00 |
| Color | 1.00 |
| Propylene Glycol | 12.00 |
| Tetrasodium Pyrophosphate | 6.58 |

(a)27.9% solution

Examples VIII and IX are prepared as follows. Start by combining water and sorbitol, if required. Add sodium fluoride and saccharin. Next, disperse the carboxymethylcellulose and xanthan gum, if required, in the glycerin, before adding to the mixture. Add the polyethylene glycol or propylene glycol and polyoxyethylene. Next add the flavor system, color solution, and sodium alkyl sulfate. Add the sodium carbonate, silica, and sodium bicarbonate. Lastly, slowly add the tetrasodium pyrophosphate and calcium peroxide, if required. Continue mixing until homogeneous. Mill and/or deareate the final product if desired for aesthetic preference.

What is claimed is:

1. A dentifrice formulation contained in physically separated compartments of a dispenser, comprising:
    a. a first dentifrice composition having an ionic strength of from about 1,000 μmho to about 50,000 μmho comprising:
        (i) from about 0.1% to about 8% of a polyoxyethylene having a molecular weight of from about 200,000 to about 7,000,000; and
        (ii) from about 92% to about 99.5% of one or more aqueous carriers; and
    b. a second dentifrice composition.

2. The dentifrice formulation according to claim 1 wherein the ionic strength of first dentifrice composition is a result of the first dentifrice composition comprising from about 4% to about 70% of a salt.

3. The dentifrice formulation according to claim 2 wherein the salt in the first dentifrice composition is sodium bicarbonate.

4. The dentifrice formulation according to claim 3 wherein the polyoxyethylene is present in an amount of from about 0.2% to about 5% and the molecular weight of the polyoxyethylene is from about 600,000 to about 2,000,000.

5. The dentifrice formulation according to claim 4 wherein the first dentifrice composition, the second dentifrice composition, or both of the dentifrice compositions further comprises a soluble fluoride source capable of providing from about 50 ppm to about 3500 ppm of free fluoride ions.

6. The dentifrice formulation according to claim 5 wherein the soluble fluoride source is sodium fluoride.

7. The dentifrice formulation according to claim 6 wherein the first dentifrice composition, the second dentifrice composition, or both of the dentifrice compositions further comprises an effective amount of one or more tartar control agents selected from the group consisting of linear polyphosphates, pyrophosphate salts, sodium tripolyphosphate, and mixtures thereof.

8. The dentifrice formulation according to claim 7 wherein the first dentifrice composition, the second dentifrice composition, or both of the dentifrice compositions further comprises an effective amount of one or more antimicrobial agents selected from the group consisting of zinc salts, triclosan, chlorhexidine, cetyl pyridinium chloride, and mixtures thereof.

9. The dentifrice formulation according to claim 8 wherein the second dentifrice composition comprises from about 0.1% to about 8% of a polyoxyethylene having a molecular weight of from about 200,000 to about 7,000,000 and from about 92% to about 99.9% of one or more aqueous carriers.

10. The dentifrice formulation according to claim 9 wherein the aqueous carriers of the first and second dentifrice compositions are materials selected from the groups consisting of abrasive polishing materials, propylene glycol, acidic compounds, calcium peroxide, buffering agent, thickening materials, humectants, water, surfactants, titanium dioxide, flavor system, coolants, sweetening agents, xylitol, coloring agents, and mixtures thereof.

11. The dentifrice formulation according to claim 10 wherein the first dentifrice composition is a dentifrice in the form of a paste and the second dentifrice composition is a dentifrice in the form of a gel.

12. An dentifrice formulation contained in physically separated compartments of a dispenser comprising:
    a. a first dentifrice composition having an ionic strength of from about 1,000 μmho to about 50,000 μmho comprising:
        (i) from about 4% to about 40% of sodium bicarbonate;
        (ii) from about 0.1% to about 8% of polyoxyethylene having a molecular weight of from about 200,000 to about 7,000,000;
        (iii) from about 1% to about 15% of a polyphosphate;
        (iv) from about 0.1% to about 30% of an alkali metal carbonate salt;
        (v) from about 0.01% to about 10% of calcium peroxide;
        (vi) from about 10% to about 70% of an abrasive polishing material;
        (vii) from about 10% to about 85% of one or more aqueous carriers;
    wherein the first dentifrice composition has a total water content of from about 5% to about 20%; and
    b. a second dentifrice composition comprising:
        (i) a soluble fluoride source capable of providing from about 50 ppm to about 3500 ppm of free fluoride ions;
        (ii) from about 10% to about 70% of a silica abrasive polishing material; and
        (iii) from about 30% to about 89% of one or more aqueous carriers.

13. A dentifrice formulation contained in physically separated compartments of a dispenser comprising:
    a. a first dentifrice composition having an ionic strength of from about 1,000 μmho to about 50,000 μmho; and
    b. a second dentifrice composition comprising:
        (i) from about 0.1% to about 8% of a polyoxyethylene having a molecular weight of from about 200,000 to about 7,000,000; and
        (ii) from about 92% to about 99.9% of one or more aqueous carriers.

14. An dentifrice formulation contained in physically separated compartments of a dispenser comprising:
   a. a first dentifrice composition having an ionic strength of from about 1,000 µmho to about 50,000 µmho comprising:
      (i) from about 4% to about 40% of sodium bicarbonate;
      (ii) from about 1% to about 15% of a polyphosphate;
      (iii) from about 0.1% to about 30% of an alkali metal carbonate salt;
      (iv) from about 0.01% to about 10% of calcium peroxide;
      (v) from about 10% to about 70% of an abrasive polishing material;
      (vi) from about 10% to about 85% of one or more aqueous carriers;
   wherein the first dentifrice composition has a total water content of from about 5% to about 20%; and
   b. a second dentifrice composition comprising:
      (i) from about 0.1% to about 8% of polyoxyethylene having a molecular weight of from about 200,000 to about 7,000,000;
      (ii) a soluble fluoride source capable of providing from about 50 ppm to about 3500 ppm of free fluoride ions; and
      (iii) from about 92% to about 99% of one or more aqueous carriers.

15. A dentifrice composition having an ionic strength of from about 1,000 µmho to about 50,000 µmho comprising:
   a. from about 0.1% to about 8% of a polyoxyethylene having a molecular weight of from about 200,000 to about 7,000,000; and
   b. from about 92% to about 99.9% of one or more aqueous carriers.

16. The dentifrice composition according to claim 15 wherein the ionic strength is a result of the dentifrice composition comprising from about 4% to about 70% of a salt.

17. The dentifrice composition according to claim 16 wherein the dentifrice composition comprises less than 1% of a polyoxyethylene-polyoxypropylene block copolymer.

18. The dentifrice composition according to claim 17 wherein the abrasive polishing materials do not flocculate around the polyoxyethylene.

19. A method for reducing the incidence of calculus on dental enamel comprising contacting the enamel surfaces in the mouth with the dentifrice composition according to claim 12.

20. A method for reducing the incidence of calculus on dental enamel comprising contacting the enamel surfaces in the mouth with the dentifrice composition according to claim 14.

* * * * *

UNITED STATES PATENT AND TRADEMARK OFFICE
CERTIFICATE OF CORRECTION

PATENT NO. : 5,820,854
DATED : October 13, 1998
INVENTOR(S) : WILLIAM MICHAEL GLANDORF It is certified that error appears in the above-indentified patent and that said Letters Patent is hereby corrected as shown below:

Column 10, line 66 (Example III), "5.0%" should be --50%--.

Column 11, line 7 (Example IV), "0.40" should be --0.45--.

Column 12, line 14 (Example VI), "4.90" should be --4.00--.

Column 15, line 20, "0. 1%" should be --0.1%--.

Signed and Sealed this

Second Day of November, 1999

Attest:

Q. TODD DICKINSON

*Attesting Officer*  *Acting Commissioner of Patents and Trademarks*